June 18, 1974 O. H. HONDA Plant Pat. 3,573
CARNATION PLANT RUBY RED SIM
Filed April 4, 1973
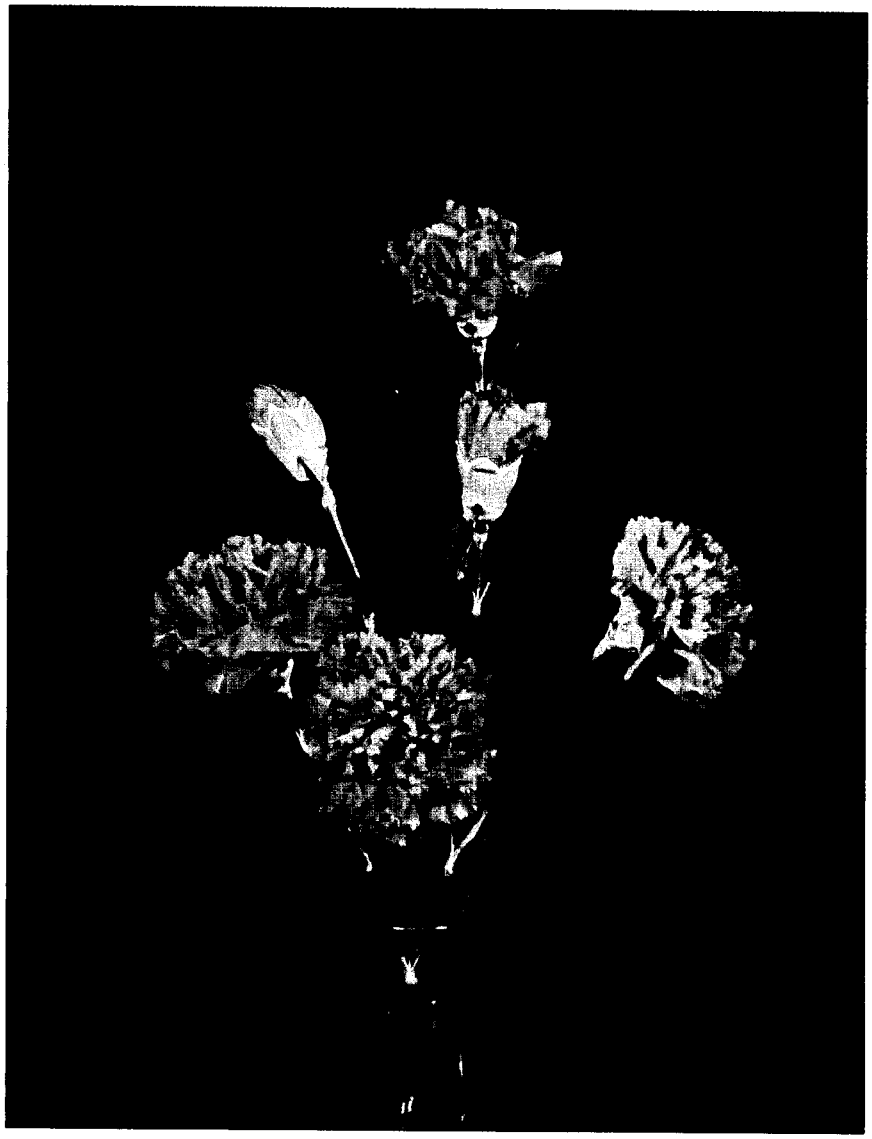

United States Patent Office

Plant Pat. 3,573
Patented June 18, 1974

3,573
CARNATION PLANT

Osamu Ham Honda, Redwood City, Calif., assignor to Woodside Nurseries Company, Redwood City, Calif.

Filed Apr. 4, 1973, Ser. No. 347,866
Int. Cl. A01h 5/00
U.S. Cl. Plt.—73 1 Claim

ABSTRACT OF THE DISCLOSURE

A new variety of red carnation plant of the large flowered greenhouse forcing or perpetual blooming type, characterized by the unique coloring of its blossoms which substantially duplicates that of the flower of the "Forever Yours" rose (P.P. 2,443).

BACKGROUND OF THE NEW PLANT

This new variety of carnation plant originated as a sport of "Better Times Sim" (unpatented), which in turn was a sport of "Persian Pink Sim" (P.P. 2,535), and was discovered by me in December 1969 in my greenhouses at Redwood City, Calif., during the course of my efforts to breed or otherwise develop improved carnation blooms for the cut flower market. The beautiful red color of the blossom of this sport led to my reproducing the sport through several generations, by means of cuttings, at Redwood City, Calif., and it was then that the consistently uniform color of the flowers was observed to be the same as that of the "Forever Yours" rose and because of the great favor of that color in the marketplace, asexual propagation of the new plant was begun in 1970–1971 to build a stock for commercial scale production of the plant. Successive generations of this plant propagated and grown in greenhouse at Redwood City, Calif., and at West Hartford, Conn., has shown the new color characteristic of its flowers to be firmly fixed and to hold true from generation to generation.

DESCRIPTION OF THE DRAWING

My new variety of carnation plant is illustrated by the accompanying drawing which shows buds and blossoms in various stages of opening and which shows the color of the flowers as nearly true as it is reasonably possible to obtain by conventional photographic procedures.

DESCRIPTION OF THE NEW PLANT

The following is a description of my new variety of carnation plant with color designations according to the H.C.C. Colour Chart (HCC) and the RHS Colour Chart (RHS) issued by The Royal Horticultural Society of London, England.

*The plant*

Origin: Sport

Parentage: "Better Times Sim" (unpatented) which originated as a sport of "Persian Pink Sim" (Plant Pat. 2,535).

Classification: Botanic—Dianthus Caryophyllus. Commercial—Sim type, greenhouse forcing.

The form, growth, flower porduction, and foliage characteristics of this new plant are the same in all ways, except blossom color, as those of the typical Sim varieties which generally have the morphological characteristics of the carnation plant originated by William Sim and described in his Plant Pat. 669.

*The flower*

The characteristics of the bud and flower of this new variety, except the color, are like those of a Sim type of carnation plant in substantially all ways. The bud is large, short and wide opening with upstanding generally ovate sepals. The flower is borne singly, is large and high centered, with a diameter of 3 to 3½ inches and with 50 to 55 petals each of which has a deeply serrated or toothed end margin to give the petals a rather frilly aspect. The fragrance of the flower is slight and the lasting quality, as a cut flower, is from 7 to 15 days, depending upon the ambient temperature.

The overall color of the flower of this new variety of carnation plant is the identical red of the "Forever Yours" rose, which is described in Plant Pat. 2,443 as having the general color effect of HCC Cardinal Red 822/3 in the newly opened flower which fades slightly to HCC Rose Red 724/1.

Many of the petals of my new flower are marked by one or more light pinkish streaks extending lengthwise of the petal on the outer half of its upper surface. The general color effect of this new flower, however, may be classified as RHS Red Group 53B to 53C, the color variation being substantially the same as is experienced with "Forever Yours" roses. The color is more intense under conditions of low sunlight and tends to become brighter as sunlight exposure increases.

I claim:

1. A new and distinct variety of carnation plant, substantially as herein shown and described, characterized by the distinctive overall red coloring of its blossoms.

No references cited.

ROBERT E. BAGWILL, Primary Examiner